United States Patent [19]
Effenberger et al.

[11] Patent Number: 4,859,784
[45] Date of Patent: Aug. 22, 1989

[54] PROCESS FOR THE PRODUCTION OF OPTICALLY ACTIVE CYANOHYDRINS

[75] Inventors: Franz Effenberger; Thomas Ziegler; Siegfried Foerster, all of Stuttgart, Fed. Rep. of Germany

[73] Assignee: Degussa Aktiengesellschaft, Frankfurt am Main, Fed. Rep. of Germany

[21] Appl. No.: 145,158

[22] Filed: Jan. 19, 1988

[30] Foreign Application Priority Data

Jan. 20, 1987 [DE] Fed. Rep. of Germany ....... 3701383

[51] Int. Cl.$^4$ ............... C07C 120/00; C07C 207/327; C07C 333/16; C07C 317/54
[52] U.S. Cl. .................................... 549/491; 546/330; 548/561; 549/75; 549/442; 549/552; 558/351
[58] Field of Search ....................... 558/351; 548/561; 549/491, 75, 552, 442; 546/330

[56] References Cited

U.S. PATENT DOCUMENTS

| 1,984,415 | 12/1934 | Macallum | 558/351 |
| 2,101,823 | 12/1937 | Dittmar | 558/351 |
| 3,850,976 | 11/1974 | Shibuya et al. | 558/351 |
| 4,554,102 | 11/1985 | Dong et al. | 558/351 X |
| 4,594,196 | 6/1986 | Stoutamire et al. | 558/351 |

FOREIGN PATENT DOCUMENTS 1300111 4/1970 Fed. Rep. of Germany .

OTHER PUBLICATIONS

Biochemische Zeitachrift 346, 301–321 (1966), "Uber das Flavinenzym D–Oxynitrilase"–Becker and Pfeil.

Primary Examiner—Joseph Paul Brust
Attorney, Agent, or Firm—Beveridge, DeGrandi & Weilacher

[57] ABSTRACT

Optically active cyanohydrins are produced by the reaction of an aldehyde with hydrocyanic acid in the presence of D-oxynitrilase (E.C.4.1.2.10). The reaction takes place in an organic solvent which is not miscible with water, but which is saturated with water or an aqueous buffer solution.

7 Claims, No Drawings

PROCESS FOR THE PRODUCTION OF OPTICALLY ACTIVE CYANOHYDRINS

INTRODUCTION AND BACKGROUND

The present invention relates to a process for the production of optically active cyanohydrins by reaction of aldehydes with hydrocyanic acid in the presence of D-oxynitrilase.

Optically active cyanohydrins serve primarily as intermediate products for the production of corresponding optically active 2-hydroxycarboxylic acids. Optically active 2-hydroxycarboxylic acids obtained thereby in turn are esterified to a large extent with chrysammic acid and then can be used in the commercially important pyrethroid insecticides. Optically active mandelic acid is then frequently used for the dissociation of racemic compounds of basic (alkaline) compositions.

It is already known from Biochemische Zeitschrfit 346, 301–321 (1966) to produce optically active cyanohydrins by reaction of aldehydes with hydrocyanic acid in the presence of D-oxynitrilase (E.C.4.1.2.10) in a 0.05M 50% alcoholic acetate buffer at a pH of 5.4.

German Pat. No. 1 300 111 of the same authors discloses that it is known to undertake this reaction in a pure aqueous 0.05M acetate buffer at a pH of 5.4, to use the D-oxynitrilase in the form of its combination with an organic ion exchanger which is insoluble in the reaction mixture, such as ECTEOLA-cellulose (reaction product of epichlorohydrin, triethanolamine and sodium cellulose) or DEAE-cellulose (diethyl aminoethyl-cellulose).

In the known process, which is carried out in a reaction medium with a high water content, numerous aldehydes can be converted into more or less high chemical yields and into more or less high optical yields of optically active cyanohydrins. Table 2 of on parge 310 of the above "Biochemische Zeitschrift 346" seems to infer, however, that numerous other aldehydes cannot be converted into optically active cyanohydrins.

SUMMARY OF THE INVENTION

In accordance with the present invention, there is provided a process for the production of optically active cyanohydrins by reaction of an aldehyde with hydrocyanic acid wherein the reaction is carried out in an organic solvent which is immiscible with water, but is saturated with water or with an aqueous buffer solution.

Aldehydes which can be converted according to the known processes into optically active cyanohydrins likewise can be reacted by the process according to the present invention with comparable or even with better yields. Moreover, using the process according to the present invention, even aldehydes can be converted into optically active cyanohydrins, which were heretofore unsuitable for use with the processes known until the present invention.

DETAILED DESCRIPTION OF THE INVENTION

The process according to the present invention is especially suitable for the conversion of aldehydes of the following general formula:

in which R is one of the following groups:

methyl, ethyl, propyl, i-propyl, butyl, i-butyl, t-butyl, pentyl, hexyl, 2-methylbutyl, heptyl, nonyl, undecyl, 1-chloro-1-methyl-ethyl, oxiranyl, vinyl, propenyl, propene-2-yl, 2-pentene-2-yl, 3-heptene-3-yl, penta-1,3-dienyl, 2,6-dimethyl-penta-1,5-dienyl, 2,6-dimethyl-penta-5-enyl, 2-phenylethyl, 1-phenylethyl, 2-phenyl ethenyl, 2-(0-nitrophenyl)-ethenyl, cyclohexene-4-yl, cyclohexyl, phenyl, o-methylphenyl, m-methylphenyl, p-methylphenyl, o-chlorophenyl, m-chlorophenyl, p-chlorophenyl, o-nitrophenyl, p-nitrophenyl, m-methoxyphenyl, p-methoxyphenyl, m-phenoxyphenyl, p-phenoxyphenyl, o-phenoxyphenyl, o-hydroxyphenyl, m-hydroxyphenyl, p-hydroxyphenyl, p-isopropyl phenyl, 3-methoxy-4-hydroxyphenyl, 3,4-dichlorophenyl, 2,4-dichlorophenyl, 2,6-dichlorophenyl, 2,3-dimethoxyphenyl, 2,4-dimethoxyphenyl, 2,5-dimethoxyphenyl, 3,4-dimethoxyphenyl, 3,4-methylene dioxyphenyl, 2,4-dihydroxyphenyl, p-dimethylamino phenyl, alpha-napthyl, 2-pyrrolyl, 2-furyl, 2-thienyl, 3-thienyl, 2-pyridyl, 3-pyridyl, 4-pyridyl, chloromethyl, dichloromethyl, trichloromethyl, fluoromethyl, difluoromethyl, trifluoromethyl or 2-methyl mercapto ethyl.

As may be seen from the above listing suitable aldehydes include those in which the R group is saturated or unsaturated aipthatic or aromatic which may contain halogen, sulfur, nitrogen, oxygen or hydroxy substituents.

The hydrocyanic acid is used in an amount at least equivalent to the amount of aldehyde which is used. However, it is advantageous to use an excess of the acid of up to approximately 5 mole equivalents.

D-oxynitrilase can be obtained from commercially available bitter almond bran. It can be used following precipitation with for example ammonium sulfate as free enzyme, which is suspended in the reaction mixture. These are matters known in the art.

Then the reaction is advantageously carried out in an enzyme-diaphragm-reactor. However, it is preferable that the D-oxynitrilase be used in immobilized form, for example, in the form of glass spheres, CE-ion exchanges, DEAE-sephadex and especially on AVICEL cellulose or ECTEOLA cellulose. Immobilization of enzymes is well known in the art.

For use in the process according to the present invention, suitable organic solvents are, for example, aliphatic hydrocarbons, such as petrol ether, hexane or cyclohexane, aromatic hydrocarbons, such as benzene or toluene, chlorinated aliphatic hydrocarbons, such as methylene chloride, chloroform or trichloroethane, ethers, such as diethyl ether, diisopropyl ether or t-butyl methyl ether, carboxylic acid alkyl esters, such as esters of formic acid, acetic acid, propionic acid, butyric acid, pentanoic acid and hexanoic acid with methyl-, ethyl-, n-propyl-, i-propyl-, n-butyl-, i-butyl-, t-butyl-, n-pentyl- and n-hexyl alcohol, and aliphatic or cycloaliphatic alcohols, such as n-butanol, n-pentanol, n-hexanol, n-octanol or cyclohexanol. Mixtures can also be used.

The organic solvent is saturated with water or preferably with an aqueous buffer solution, especially a solution suitable to obtain the pH range of between 3 and 8.

Suitable buffer solutions are for example 0.001–1.0 molar solutions of sodium acetate and acetic acid, sodium or potassium dihydrogen phosphate with sodiunm or potassium hydroxide solution or phosphoric acid, tris-(hydroxymethyl)-aminomethane and hydrochloric acid, boric acid and sodium hydroxide, citronic acid and sodium hydroxide.

The aldehyde can react with the hydrocyanic acid under a wide range of temperature conditions, typically between 0° and 90° C., and preferably at room temperature.

It has been surprisingly found that the crude solutions of optically active cyanohydrins obtained by the process according to the present invention can be obtained very well. It is not necessary that the crude solutions be purified or treated any further, but can be directly used in further processes under certain conditions, for instance by hydrolysis into the corresponding optically active 2-hydroxycarboxylic acids.

If the D-oxynitrilase is to be used in the immobilized form, it is added to the carrier material in the form of an aqueous solution. Following drying in air, the immobilized enzyme is ready for use as catalyst.

The implementation of an embodiment of the process according to the invention can take place in such a manner that the enzyme or the catalyst preparation which is produced therewith is suspended or slurried in ethyl acetate, which is saturated with an 0.01M acetate buffer for a pH of 5.4. The suspension or slurry is then used with the aldehyde and subsequently with the hydrocyanic acid, or else as a solution in ethyl acetate. Following completion of the reaction, the undissolved components of the reaction mixture are filtered out and the filtrate is dried, for instance over sodium sulfate. Following repeated filtration and evaporation of the solvent under decreased pressure, the optically active cyanohydrin remains as a colorless to pale yellow oil.

The invention is further described by the following illustrative examples. For the exact determination of the enantiomeric yield, a sample of the cyanohydrin which is formed is converted by means of R(+)-methoxyl trifluoromethyl phenyl acetyl chloride into the R(+)-MTPA ester and this is separated by capillary gas chromatography into the two diastereo isomers. The diastereo isomer excess is shown in the following examples in percentages.

EXAMPLE 1

2.0 grams of AVICEL cellulose (Manufacturer: Merck, Darmstadt) were swelled in 20 ml aqeuous 0.01M acetate buffer for pH 5.4 for 2 hours, then were suctioned off and pressed. Following repeated slurrying in 50 ml of the same buffer solution, 150 µl of a D-oxynitrilase solution containing 700 units of D-oxynitrilase/ml ($A_{sp}=65$ units/mg) was added dropwise with agitation into 0.020M acetate buffer for pH 5.4. Stirring was carried out for 1 hour at room temperature, then the impregnated cellulose was separated out, pressed and dried.

The catalyst preparation was suspended in 25.0 ml ethyl acetate saturated with 0.01M acetate buffer for pH 5.4, and the suspension was used sequentially with 0.53 g (5 m Moles benzaldehyde and 250 µl (6.5 m Moles) of hydrocyanic acid. It was stirred for 2.5 hours at room temperature, then the catalyst was filtered out and the filtrate was dried over sodium sulfate. Following filtration and evaporation of the solvent under decreased pressure, 0.63 g (95% of theory) of mandelonitrile remained as a colorless oil.

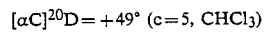

Diastereo isomer excess: 99.3%.
$^1$H-NMR (CDCl$_3$): 7.50 (s, H$^{arom}$, 5H), 5.50 (s, —CH—CN, 1H), 3.78 (s, OH, 1H).

EXAMPLE 2

5.0 grams of ECTEOLA cellulose (Manufacturer: Macherey, Nagel and Co., Dueren) were swelled in 150 ml of aqueous 0.01M acetate buffer for pH 5.4 for 2 hours, then were suctioned off and pressed. Following repeated slurrying in 50 ml of the same buffer, a D-oxynitrilase solution (1.5 mg of D-oxynitrilase, $A_{sp}=60$ units/mg in 0.5 ml of 0.025M phosphate buffer for pH 7.0) was added dropwise with stirring at room temperature. It was stirred for 1 hour at room temperature, then the impregnated cellulose was separated off, pressed and dried.

The catalyst preparation was suspended in 40 ml ethyl acetate saturated with 0.01M acetate buffer for pH 5.4. The suspension was used in sequence with 1.36 g (10 m Moles) of m-methoxyl benzaldehyde and 1 ml of a mixture of hydrocyanic acid and ethyl acetate in a volume ratio of 1:1 (13 m Moles of HCN). Stirring was conducted for 1.5 hours at room temperature, then the catalyst was filtered off and the filtrate was dried over sodium sulfate. Following filtration and evaporation of the solvent under reduced pressure, 1.55 g (95% of theory) of m-methoxy mandelonitrile remained as a pale yellow oil.

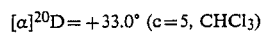

Diastereo isomer excess: 90%.
$^1$H-NMR(CDCl$_3$): 6.82–7.50 (m, H$^{arom}$, 4H), 3.82 (s, OCH$_3$, 3H), 5.50 (s, OH, 1H), 4.05 (s, OH, 1H).

EXAMPLE 3

As in Example 1, 0.99 grams (5 m Moles) of m-phenoxy benzaldehyde were reacted in 50 ml of reaction medium for a reaction time of 8 days. After the treatment, 1.12 grams (99% of theory) of m-phenoxy mandelonitrile remained as a yellowish oil.

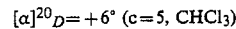

Diastereo isomer excess: 98%.
$^1$H-NMR (DCDl$_3$): 7.60–6.90 (m, H$^{arom}$, 9H), 5.50 (s, —CH—CN, 1H), 3.95 (s, OH, 1H).

EXAMPLE 4

As in Example 1, 0.48 grams (5 m Moles) of furfural were reacted for a rection time of 4 hours. Following the treatment, 0.54 grams (88% of theory) of alpha-hydroxyl-(2-furyl)-acetonitrile remained as a yellowish oil.

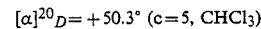

Diastereo isomer excess: 98.5%.
$^1$H-NMR (CDCl$_3$): 6.60–6.30 (m, H$^{furan}$, 2H), 7.42 (mc, H$^{furan}$, 1H), 5.50 (s, —CH—CN, 1H), 4.00 (s, OH, 1H).

EXAMPLE 5

As in example 2, 1.32 grams (10 m Moles) of cinnamaldehyde were reacted for a reaction time of 11 days. Following the treatment, 1.48 grams (93% of theory) of 2-hydroxyl-4-phenyl-3-buteric acid nitrile remained as white solid material.
Diastereo isomer excess: 45%.

$[\alpha]^{20}_D = +11.3°$ (C=5, CHCl$_3$),

Melting point: 65°–70° C.
Following recrystallization from n-hexane:

$[\alpha]^{20}_D = +3.7°$ (c=5, CHCl$_3$)

Diastereo isomer excess: 31%.
Melting point: 76°–77° C.
$^1$H-NMR (CDCl$_3$): 7.47 (s, H$^{arom}$ 5H), 6.45 (d, Ph—CH=, 1H), 6.20 (d=CH—CH—CN, 1H), 5.25 (d, —CH—CN, 1H), 3.80 (s, OH, 1H).
Literature:
Melting point: 75° C., G. Peine, Chem. Ber. 17, 2113 (1884).

EXAMPLE 6

As in Example 1, 0.35 grams (5 m Moles) of crotonaldehyde were reacted for a reaction time of 3 hours. Following the treatment, 0.33 grams (68% of theory) of 2-hydroxyl-3-pentene acid-nitrile remained as a yellowish oil.

$[\alpha]^{20}_D = 24.7°$ (c=5, CHCl$_3$)

Diastereo isomer excess: 97%.
$^1$H-NMR (CDCl$_3$): 6.30–5.40 (m, =CH, 2H), 4.95 (d, —CH—CN, 1H), 3.50 (s, OH, 1H), 1.80 (d, CH$_3$, 3H).

EXAMPLE 7

As in Example 2, 0.43 grams (5 m Moles) of pivaldehyde were reacted for a reaction time of 4.5 hours. Following the treatment, 0.44 grams (78% of theory) of 3,3-dimethyl-2-hydroxyl-butanoic acid nitrile remained as a colorless oil.

$[\alpha]^{20}_D = +11.1°$ (c=5, CHCl$_3$)

Diastereo isomer excess: 73%.
$^1$H-NMR (CDCl$_3$): 4.14 (s, —CH—CN, 1H), 3.25 (s, OH, 1H), 1.10 (s, CH$_3$, 9H).

EXAMPLE 8

As in Example 1, 0.60 grams (5 m Moles) of phenyl acetaldehyde were reacted for a reaction time of 4.5 hours. Following the treatment, 0.70 grams (95% of theory) of phenyllactic acid nitrile remained as a yellowish oil.

$[\alpha]^{20}_D = +2.0°$ (c=5, CHCl$_3$)

Diastereo isomer excess: 40%.
$^1$H-NMR (CDCl$_3$): 7.37 (s, H$^{arom}$, 5H), 4.60 (t, —CH—CN, 1H), 3.40 (s, OH, 1H), 3.10 (d, CH$_2$, 2H).

EXAMPLE 9

As in Example 1, 0.52 grams (5 m Moles) of 3-methyl mercapto-propionaldehyde were reacted for a reaction time of 6.5 hours. Following the recovery treatment, 0.64 grams (97% of theory) of 2-hydroxyl-4-methyl mercapto-butyric acid nitrile remained as a yellowish oil.

$[\alpha]^{20}_D = +21.5°$ (c=5, CHCl$_3$)

Diastereo isomer excess: 80%.
$^1$H-NMR (CDCl$_3$): 4.80 (t, —CH—CN, 1H), 3.72 (s, OH, 1H), 2.80 (dt, CH$_2$—CH—CN, 2H), 2.29 (t, —S—CH$_2$—, 2H), 2.22 (s, H$_3$C—S—, 3H).

EXAMPLE 10

As in Example 1, 0.28 grams (5 m Moles) of acrolein were reacted for a reaction time of 6 hours. Following the treatment, 0.24 grams (58% of theory) of 2-hydroxybutyric-3-acid nitrile remained as a colorless oil.

$[\alpha]^{20}_D = -0.5°$ (c=5, CHCl$_3$)

Diastereo isomer excess: 12%.
$^1$H-NMR (CDCl$_3$): 6.34–5.40 (m, =CH, 3H), 5.10 (d, —CH—CN, 1H), 3.68 (s, OH, 1H).

EXAMPLE 11

As in Example 1, 0.36 grams (5 m Moles) of butyraldehyde were reacted for a reaction time of 4.5 hours. Following recovery, 0.37 grams (75% of theory) of 2-hydroxyl pentanoic acid nitrile remained as a colorless oil.

$[\alpha]^{20}_D = +13.1°$ (c=5, CHCl$_3$)

Diastereo isomer excess: 96%.
$^1$H-NMR (CDCl$_3$): 1.2 (d, CH$_3$, 3H), 1.6 (m, CH$_2$, 4H), 4.6 (t, CH, 1H), 4.0 (s, CH, 1H).

Further variations and modifications will become apparent from the foregoing and are intended to be encompassed by the claims appended hereto.

German priority application P 37 01 383.1 is relied on and incorporated herein by reference.

We claim:

1. A process for the production of an optically active cyanohydrin comprising reacting an aldehyde with hydrocyanic acid in the presence of D-oxynitrilase and an organic solvent which is immiscible with water, said solvent being saturated with water or being saturated with an aqueous buffer solution.

2. The process according to claim 1, wherein the solvent is an aliphatic or aromatic hydrocarbon, a chlorinated aliphatic hydrocarbon, an ether, a carboxylic acid alkyl ester or an aliphatic or cycloaliphatic alcohol.

3. The process according to claim 1, wherein the organic solvent is saturated with an aqueous buffer solution for the pH range of between 3 and 8.

4. The process according to claim 1, wherein the D-oxynitrilase is immobilized on a carrier therefor.

5. The process according to claim 4 wherein the carrier is in the form of glass spheres or an organic ion exchanger which is insoluble in the reaction mixture.

6. The process according to claim 5, wherein the organic ion exchanger carrier is in the form of a cellulose product.

7. The process according to claim 1, wherein the D-oxynitrilase is in a slurry in an organic solvent and the slurry is then mixed with said aldehyde and the hydrocyanic acid.

* * * * *